US010125115B2

United States Patent
Bhirud et al.

(10) Patent No.: US 10,125,115 B2
(45) Date of Patent: Nov. 13, 2018

(54) PROCESS FOR THE PREPARATION OF EFINACONAZOLE

(71) Applicant: Glenmark Pharmaceuticals Limited, Mumbai (IN)

(72) Inventors: Shekhar Bhaskar Bhirud, Mumbai (IN); Samir Naik, Mumbai (IN); Sushanta Mishra, Orissa (IN); Abhijit Pardeshi, Pune (IN); Sri Hari Galla, Vijayawada (IN); Suresh Babu Narayanan, Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/577,818

(22) PCT Filed: Jun. 1, 2016

(86) PCT No.: PCT/IB2016/053209
§ 371 (c)(1),
(2) Date: Nov. 29, 2017

(87) PCT Pub. No.: WO2016/193917
PCT Pub. Date: Dec. 8, 2016

(65) Prior Publication Data
US 2018/0162833 A1   Jun. 14, 2018

(30) Foreign Application Priority Data

Jun. 4, 2015  (IN) .................. 2158/MUM/2015

(51) Int. Cl.
*C07D 401/06* (2006.01)
*C07C 69/78* (2006.01)

(52) U.S. Cl.
CPC ............ *C07D 401/06* (2013.01); *C07C 69/78* (2013.01)

(58) Field of Classification Search
CPC .................................................. C07D 401/06
USPC .......................................................... 546/210
See application file for complete search history.

(56) References Cited

U.S. PATENT DOCUMENTS

2013/0150586 A1   6/2013   Mimura

*Primary Examiner* — Patricia L Morris
(74) *Attorney, Agent, or Firm* — Ryan, Mason & Lewis, LLP

(57) ABSTRACT

The present invention relates to a process for the preparation of Efinaconazole and salts thereof.

7 Claims, 2 Drawing Sheets

Glenmark pharmaceuticals Limited

PROCESS FOR THE PREPARATION OF EFINACONAZOLE

PRIORITY

This application claims the benefit of Indian Provisional Application 2158/MUM/2015 filed on Jun. 4, 2015, entitled "PROCESS FOR PREPARATION OF EFINACONAZOLE", the contents of which are incorporated herein by reference.

FIELD OF INVENTION

The present invention relates to process of preparation of efinaconazole.

BACKGROUND OF THE INVENTION

Efinaconazole which is chemically known as (2R,3R)-2-(2,4-difluorophenyl)-3-(4-methylene piperidin-1-yl)-1-(1H-1,2,4-triazol-1-yl)butan-2-ol is represented by a compound of formula I,

1.

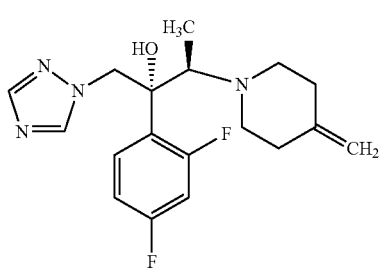

I

Efinaconazole marketed as JUBLIA® is a topical solution, 10% and is indicated for the topical treatment of onchomycosis of toenail (s) due to *trichophyton rubrum* and *trichophyton mentagrophytes*.

Various synthetic processes for preparation of efinaconazole are known in the art. The present invention provides a novel process for preparation of efinaconazole which provides a better purity profile and which can be easily performed on industrial scale.

SUMMARY OF THE INVENTION

The present invention provides a process for the preparation of (2R,3R)-2-(2,4-difluorophenyl)-3-(4-methylenepiperidin-1-yl)-1-(1H-1,2,4-triazol-1-yl)butan-2-ol [efinaconazole], a compound of formula I, comprising:

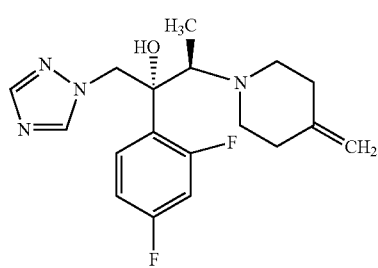

I a) reacting (2R,3 S)-2-(2,4-difluorophenyl)-3-methyl-2-[(1H-1,2,4-triazol-1-yl) methyl] oxirane, a compound of formula II, with 4-methylenepiperidine, a compound of formula III or salt thereof to obtain crude efinaconazole;

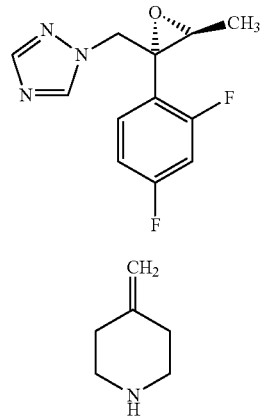

b) reacting the crude efinaconazole obtained from step 'a' with an acid selected from the group consisting of an inorganic acid, an organic carboxylic acid and an optically active acid to obtain a reaction mixture containing an acid addition salt of (2R,3R)-2-(2,4-difluorophenyl)-3-(4-methylene piperidin-1-yl)-1-(1H-1,2,4-triazol-1-yl)butan-2-ol;

c) separating the acid addition salt of (2R,3R)-2-(2,4-difluorophenyl)-3-(4-methylene piperidin-1-yl)-1-(1H-1,2,4-triazol-1-yl)butan-2-ol from the reaction mixture; and d) converting the acid addition salt of (2R,3R)-2-(2,4-difluorophenyl)-3-(4-methylene piperidin-1-yl)-1-(1H-1,2,4-triazol-1-yl)butan-2-ol) to (2R,3R)-2-(2,4-difluorophenyl)-3-(4-methylene piperidin-1-yl)-1-(1H-1,2,4-triazol-1-yl)butan-2-ol.

In one embodiment, the present invention provides Di-toluoyl-D-tartaric acid salt of (2R,3R)-2-(2,4-difluorophenyl)-3-(4-methylene piperidin-1-yl)-1-(1H-1,2,4-triazol-1-yl)butan-2-ol, a compound of formula VII or Di-toluoyl-L-tartaric acid salt of (2R,3R)-2-(2,4-difluorophenyl)-3-(4-methylene piperidin-1-yl)-1-(1H-1,2,4-triazol-1-yl)butan-2-ol, a compound VIII.

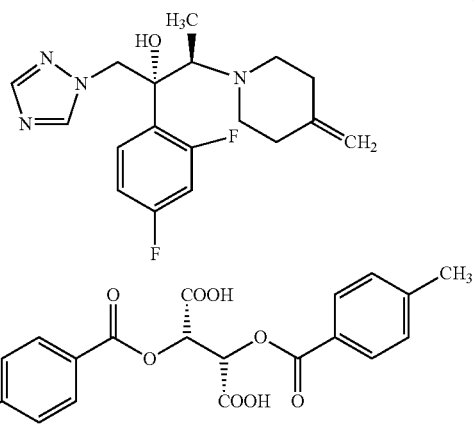

VII

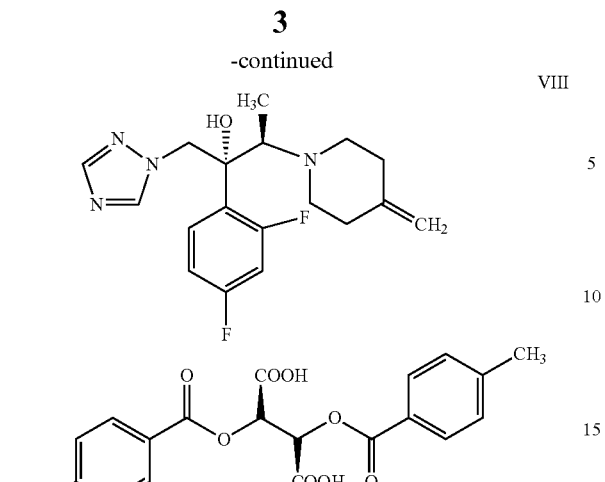

VIII

In one embodiment, the present invention provides a process for the preparation of D-di-toluoyl tartaric acid salt of (2R,3R)-2-(2,4-difluorophenyl)-3-(4-methylene piperidin-1-yl)-1-(1H-1,2,4-triazol-1-yl)butan-2-ol or L-di-toluoyl tartaric acid salt of (2R,3R)-2-(2,4-difluorophenyl)-3-(4-methylene piperidin-1-yl)-1-(1H-1,2,4-triazol-1-yl) butan-2-ol comprising reacting crude efinaconazole with D-di-toluoyl tartaric acid or with L di-toluoyl tartaric acid to obtain D-di-toluoyl tartaric acid salt of (2R,3R)-2-(2,4-difluorophenyl)-3-(4-methylene piperidin-1-yl)-1-(1H-1,2,4-triazol-1-yl)butan-2-ol, a compound of formula VII or L-di-toluoyl tartaric acid salt of (2R,3R)-2-(2,4-difluorophenyl)-3-(4-methylenepiperidin-1-yl)-1-(1H-1,2,4-triazol-1-yl)butan-2-ol, a compound of formula VIII.

In one embodiment, the present invention provides a process for the preparation of crystalline (2R,3R)-2-(2,4-difluorophenyl)-3-(4-methylene piperidin-1-yl)-1-(1H-1,2,4-triazol-1-yl)butan-2-ol, the compound of formula I comprising:

a) treating (2R,3R)-2-(2,4-difluorophenyl)-3-(4-methylenepiperidin-1-yl)-1-(1H-1,2,4-triazol-1-yl) butan-2-ol with a solvent to obtain a reaction mixture;

b) optionally, adding an anti-solvent; and c) isolating (2R,3R)-2-(2,4-difluorophenyl)-3-(4-methylenepiperidin-1-yl)-1-(1H-1,2,4-triazol-1-yl)butan-2-ol from the above step 'a' or step 'b' wherein the solvent is selected from the group consisting of C1-C5 alcohol, nitrile, water, sulfoxides, hydrocarbons, esters, ethers, amides, chlorinated hydrocarbon and mixtures thereof.

In one embodiment, the present invention provides use of a salt of (2R,3R)-2-(2,4-difluorophenyl)-3-(4-methylenepiperidin-1-yl)-1-(1H-1,2,4-triazol-1-yl)butan-2-ol for obtaining (2R,3R)-2-(2,4-difluorophenyl)-3-(4-methylenepiperidin-1-yl)-1-(1H-1,2,4-triazol-1-yl) butan-2-ol wherein the content of (2S,3S) isomer of efinaconazole, a compound of formula IV and/or (2R,3S) isomer of efinaconazole, the compound of formula V and/or (2S,3R) isomer of efinaconazole, the compound of formula VI is less than 0.5% w/w with respect to (2R,3R)-2-(2,4-difluorophenyl)-3-(4-methylenepiperidin-1-yl)-1-(1H-1,2,4-triazol-1-yl)butan-2-ol as determined by HPLC.

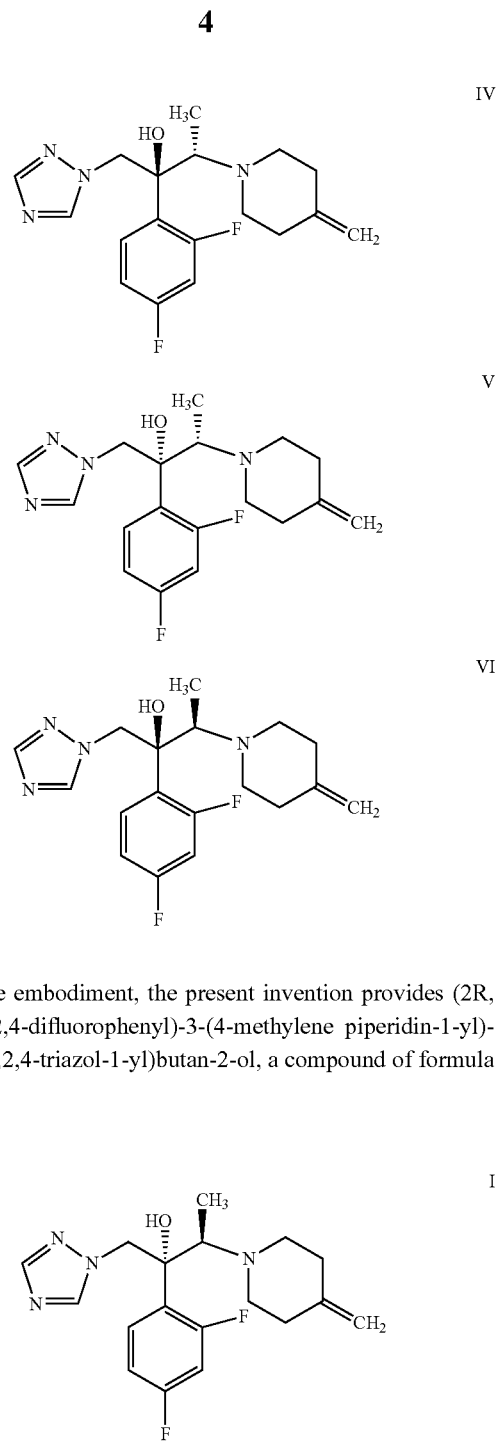

In one embodiment, the present invention provides (2R,3R)-2-(2,4-difluorophenyl)-3-(4-methylene piperidin-1-yl)-1-(1H-1,2,4-triazol-1-yl)butan-2-ol, a compound of formula I wherein the content of (2S,3S) isomer of efinaconazole, a compound of formula IV and/or (2R,3S) isomer of efinaconazole, a compound of formula V and/or (2S,3R) isomer of efinaconazole, a compound of formula VI is less than 0.5% w/w with respect to (2R,3R)-2-(2,4-difluorophenyl)-3-(4-methylene piperidin-1-yl)-1-(1H-1,2,4-triazol-1-yl)butan-2-ol, a compound of formula I, as determined by HPLC.

In one embodiment, the present invention provides a process for the preparation of (2R,3R)-2-(2,4-difluorophenyl)-3-(4-methylene piperidin-1-yl)-1-(1H-1,2,4-triazol-1-yl) butan-2-ol, the compound of formula I

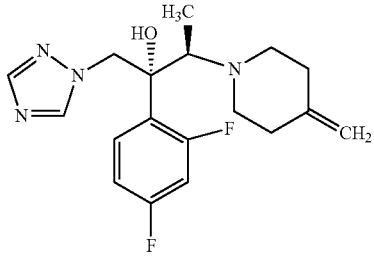

I

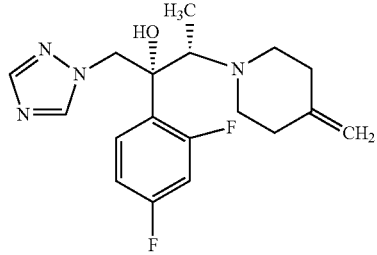

V

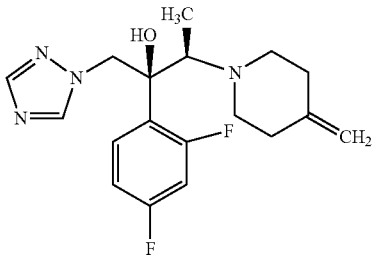

VI comprising reacting (2R,3S)-2-(2,4-difluorophenyl)-3-methyl-2-[(1H-1,2,4-triazol-1-yl)methyl]oxirane, a compound of formula II, with 4-methylenepiperidine, a compound of formula III or salt thereof in the presence of a Lewis acid.

In one embodiment, the present invention provides a method for preparing efinaconazole, or salt thereof, suitable for pharmaceutical use, comprising the steps of:

a) providing a batch of efinaconazole or a salt thereof;

b) assessing the purity of said batch of efinaconazole or salt thereof, by using at least one compound selected from the group consisting of IX, X, II, V and VI as a reference marker to determine the level of the reference marker compound; and c) selecting the batch of efinaconazole only if the percentage of the reference marker compound is less than 0.15% w/w as determined by HPLC wherein in compound IX when i) R is 2,4-difluoro, G is selected from the group consisting of hydroxy, 4-methylenepiperidine-N-oxide and amino; ii) when G is 4-methylenepiperidine, R is selected from the group consisting of 4-fluorine and H.

In one embodiment, the present invention provides a method of assessing the purity of efinaconazole and pharmaceutical compositions thereof comprising the steps of:

a) providing a standard solution of at least one of the reference marker compound selected from the group consisting of IX, X. II, V and VI

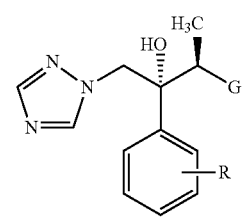

IX

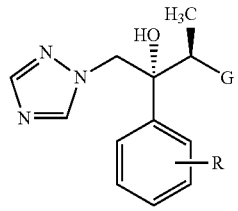

IX

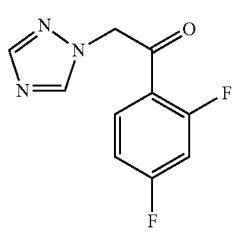

X

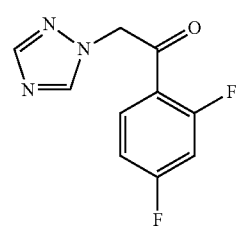

X

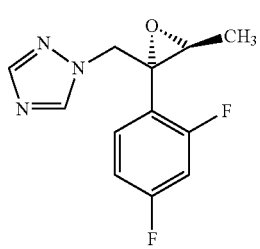

II

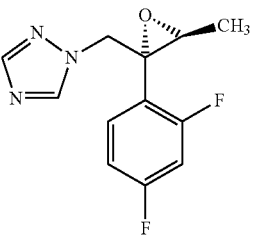

II

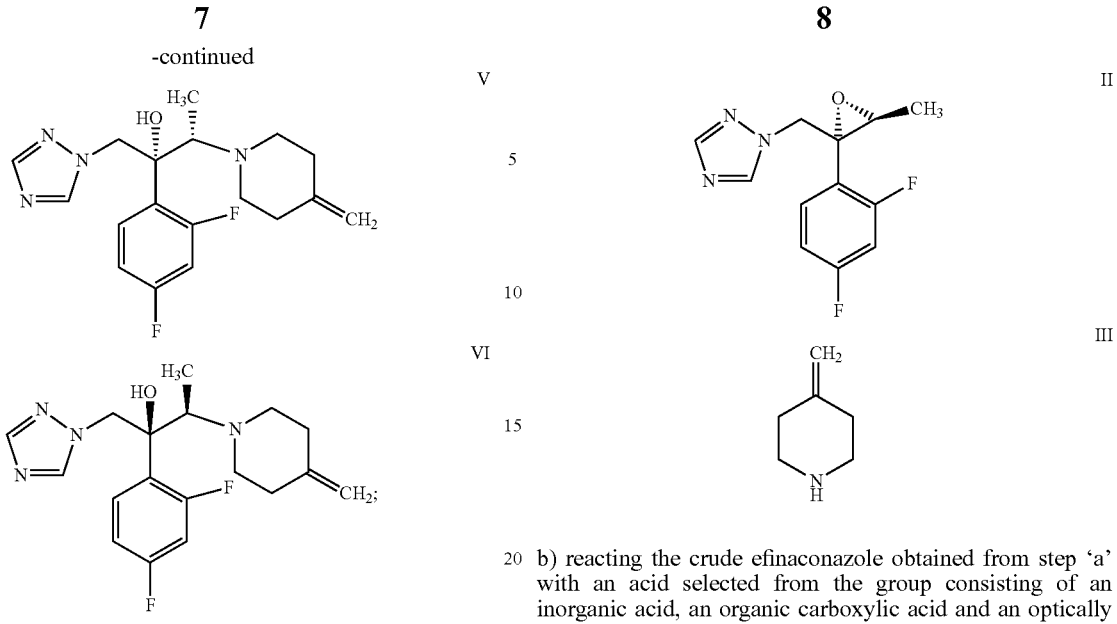

and (b) using the solution as a reference marker to determine the level of the compound reference marker compound.

BRIEF DESCRIPTION OF THE DRAWINGS

FIG. 2: XRD pattern of Di-L-toluoyl tartaric acid salt of (2R,3R)-2-(2,4-difluorophenyl)-3-(4-methylene piperidin-1-yl)-1-(1H-1,2,4-triazol-1-yl)butan-2-ol according to example 6a.

DETAILED DESCRIPTION OF THE INVENTION

Figure 1:
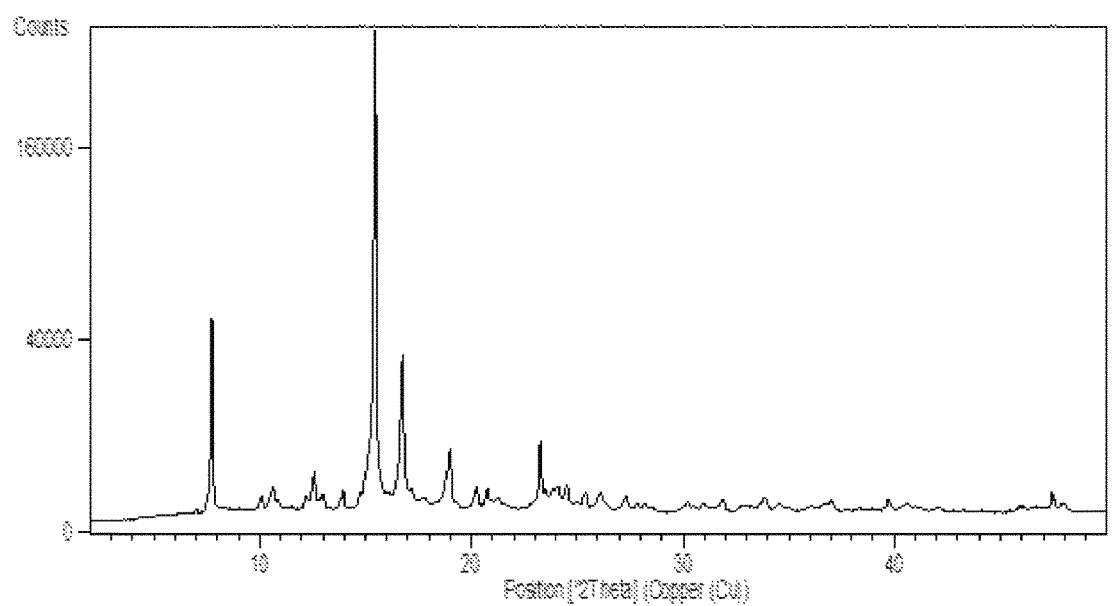
FIG. 1: XRD pattern of (2R,3R)-2-(2,4-difluorophenyl)-3-(4-methylene piperidin-1-yl)-1-(1H-1,2,4-triazol-1-yl)butan-2-ol according to example 6b.

In one embodiment, the present invention provides a process for the preparation of (2R,3R)-2-(2,4-difluorophenyl)-3-(4-methylenepiperidin-1-yl)-1-(1H-1,2,4-triazol-1-yl)butan-2-ol) [efinaconazole], a compound of formula I comprising:

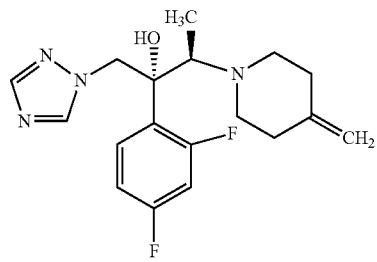

a) reacting (2R,3S)-2-(2,4-difluorophenyl)-3-methyl-2-[(1H-1,2,4-triazol-1-yl)methyl]oxirane, a compound of formula II, with 4-methylenepiperidine, a compound of formula III or salt thereof to obtain crude efinaconazole;

b) reacting the crude efinaconazole obtained from step 'a' with an acid selected from the group consisting of an inorganic acid, an organic carboxylic acid and an optically active acid to obtain a reaction mixture containing an acid addition salt of (2R,3R)-2-(2,4-difluorophenyl)-3-(4-methylene piperidin-1-yl)-1-(1H-1,2,4-triazol-1-yl)butan-2-ol;

c) separating the acid addition salt of (2R,3R)-2-(2,4-difluorophenyl)-3-(4-methylene piperidin-1-yl)-1-(1H-1,2,4-triazol-1-yl)butan-2-ol from the reaction mixture; and d) converting the acid addition salt of (2R,3R)-2-(2,4-difluorophenyl)-3-(4-methylene piperidin-1-yl)-1-(1H-1,2,4-triazol-1-yl)butan-2-ol to (2R,3R)-2-(2,4-difluorophenyl)-3-(4-methylene piperidin-1-yl)-1-(1H-1,2,4-triazol-1-yl)butan-2-ol.

In one embodiment, the term 'crude efinaconazole' refers to efinaconazole obtained by the reaction of compound of formula II with the compound of formula III or a salt thereof.

In one embodiment, the term 'crude efinaconazole' is defined as a substance having a purity in the range of about 50-95% as determined by HPLC.

In one embodiment, the term 'crude efinaconazole' is defined as a substance wherein the content of impurities is greater than 0.5% w/w with respect to efinaconazole as determined by HPLC.

In one embodiment, the term 'crude efinaconazole' is defined as a substance wherein the content of chemical impurities is greater than 0.5% w/w with respect to efinaconazole as determined by HPLC.

In one embodiment, crude efinaconazole is defined as a substance wherein the content of (2S,3S) isomer of efinaconazole, a compound of formula IV, and/or (2R,3S) isomer of efinaconazole, a compound of formula V and/or (2S,3R) isomer of efinaconazole, a compound of formula VI, is greater than 0.5% w/w with respect to efinaconazole as determined by HPLC.

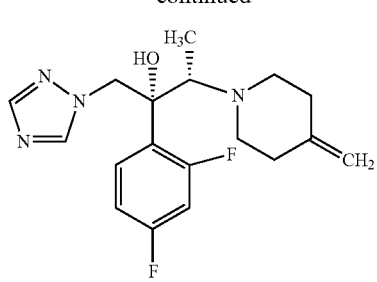

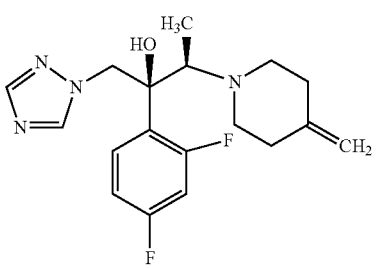

In one embodiment, the content of (2S,3S) isomer of efinaconazole, a compound of formula IV and/or (2R,3 S) isomer of efinaconazole, a compound of formula V and/or (2S,3R) isomer of efinaconazole, a compound of formula VI, in the efinaconazole obtained by the above process is less than 0.5% w/w with respect to efinaconazole as determined by HPLC.

In one embodiment, in step 'a' of the above process the reaction of compound of formula II with the compound of formula III or a salt thereof is carried out in presence of a Lewis acid.

The Lewis acid may be selected from the group consisting of lithium bromide, boron trifluoride etherate, zinc chloride, ferric chloride, aluminium chloride, lithium perchlorate and stannic chloride, copper(II) trifluoromethanesulfonate, zinc acetate, zinc trifluoromethanesulfonate. Preferably, the Lewis acid is lithium bromide.

In one embodiment, in step 'a' of the above process the reaction of compound of formula II with compound of formula III or a salt thereof is carried out in presence of a solvent.

In one embodiment, in step 'a' of the above process the reaction of compound of formula II with the compound of formula III or a salt thereof is carried out in presence of a Lewis acid in a suitable solvent to obtain crude efinaconazole.

The solvent may be selected from the group consisting of chlorinated solvents such as methylene dichloride, ethylene dichloride, chloroform, carbon tetrachloride; ethers such as diethyl ether, methyl tertiary butyl ether, di-isopropyl ether, tetrahydrofuran; nitriles such as acetonitrile, propionitrile; esters such as ethyl acetate, butyl acetate, isopropyl acetate; hydrocarbons such as, cyclohexane, toluene, xylene, hexane; alcohols such as methanol, ethanol, butanol, isopropanol, n-propanol; sulfoxides such as dimethyl sulfoxide; amides such as dimethyl formamide, dimethyl acetamide; ketones such as acetone, methyl ethyl ketone, methyl isobutyl ketone; water and or mixtures thereof. Preferably, the solvent is toluene.

In one embodiment, in step 'a' of the above process the reaction of compound of formula II with the compound of formula III or a salt thereof is carried out in presence of a phase transfer catalyst.

The phase transfer catalyst may be selected from the group consisting of benzyltrimethylammonium chloride, hexadecyltributyl phosphonium bromide, tetrabutyl ammonium hydrogen sulphate, tetrabutylammonium bromide, methyltrioctyl ammonium chloride, crown ethers, polyethylene glycols. Preferably, the phase transfer catalyst is tetrabutylammonium bromide.

In one embodiment, in step 'a' of the above process the reaction of compound of formula II with the compound of formula III is carried out in presence of a Lewis acid and a phase transfer catalyst in a suitable solvent to obtain crude efinaconazole.

In one embodiment, in step 'a' of the above process the reaction of compound of formula II with the compound of formula III is carried out in presence of a Lewis acid in a suitable solvent to obtain crude efinaconazole wherein the 4-methylenepiperidine, the compound of formula III is obtained by reacting a salt of 4-methylenepiperidine with a base.

Suitable base may be selected from the group consisting of organic bases or inorganic bases. Inorganic bases may be selected from the group consisting of hydroxides such as sodium hydroxide, potassium hydroxide, calcium hydroxide, lithium hydroxide; carbonate such as of sodium carbonate, potassium carbonate, calcium carbonate, lithium carbonate; alkoxide such as sodium methoxide, potassium methoxide; bicarbonates such as sodium bicarbonate, potassium bicarbonate, lithium bicarbonate; ammonia and the like. Organic bases may be selected from the group consisting of organic amines such as triethylamine, diisopropylethylamine, N,N-dimethylaniline, pyridine, 2-bromopyridine, 4-dimethylaminopyridine, Di-tert-butyl pyridine, 2,6-Di-tert-butyl-4-methylpyridine, N-methylmorpholine, 2,6-Lutidine, imidazole.

In one embodiment, the crude efinaconazole obtained by the reaction of compound of formula II with the compound of formula III may be purified from a solvent selected from the group consisting of chlorinated solvents such as methylene dichloride, ethylene dichloride, chloroform, carbon tetrachloride; ethers such as diethyl ether, methyl tertiary butyl ether, di-isopropyl ether, tetrahydrofuran; nitriles such as acetonitrile, propionitrile; esters such as ethyl acetate, butyl acetate, isopropyl acetate; hydrocarbon such as, cyclohexane, toluene, xylene, hexane; alcohols such as methanol, ethanol, butanol, isopropanol, n-propanol; sulfoxides such as dimethyl sulfoxide; amides such as dimethyl formamide, dimethyl acetamide; ketones such as acetone, methyl ethyl ketone, methyl isobutyl ketone; water and or mixtures thereof.

In one embodiment, in step 'b' of the above process the crude efinaconazole obtained from step 'a' is reacted with an acid selected from the group consisting of an inorganic acid, an organic carboxylic acid and an optically active acid to obtain an acid addition salt of (2R,3R)-2-(2,4-difluorophenyl)-3-(4-methylene piperidin-1-yl)-1-(1H-1,2,4-triazol-1-yl)butan-2-ol.

In one embodiment, the inorganic acid is selected from the group consisting of hydrochloric acid, hydrobromic acid, nitric acid, sulfuric acid, phosphoric acid or mixture thereof.

In one embodiment, the organic carboxylic acid is selected from the group consisting of acetic acid, trifluoroacetic acid, propionic acid, butyric acid, acrylic acid, methacrylic acid, crotonic acid, pyruvic acid, maleic acid, oxalic acid and dihydroxyfumaric acid.

In one embodiment, optically active acid is selected from the group consisting of mandelic acid, tartaric acid, camphor sulfonic acid, dibenzoyltartaric acid, di-p-toluoyl tartaric acid, glutamic acid, malic acid, aspartic acid, mucic acid, pyruglutamic acid, glucoronic acid, camphoric acid, gluconic acid, lactic acid, pantothenic acid, phenylpropionic acid, N-acetylphenyl alanine, diacetyl tartaric acid, tosyl glutamic acid, camphanic acid.

In one embodiment, in step 'b' of the above process the crude efinaconazole obtained from step 'a' is reacted with an optically active acid to obtain an acid addition salt of (2R,3R)-2-(2,4-difluorophenyl)-3-(4-methylene piperidin-1-yl)-1-(1H-1,2,4-triazol-1-yl)butan-2-ol.

In one embodiment, in step 'b' of the above process the crude efinaconazole is reacted with Di-toluoyl-L-tartaric acid to obtain reaction mixture containing Di-toluoyl-L-tartaric acid salt of (2R,3R)-2-(2,4-difluorophenyl)-3-(4-methylene piperidin-1-yl)-1-(1H-1,2,4-triazol-1-yl)butan-2-ol, impurities, isomers of efinaconazole or salt thereof.

In one embodiment, step 'c' of the above process involves separating the acid addition salt of (2R,3R)-2-(2,4-difluorophenyl)-3-(4-methylene piperidin-1-yl)-1-(1H-1,2,4-triazol-1-yl)butan-2-ol from the reaction mixture containing the acid addition salt of (2R,3R)-2-(2,4-difluorophenyl)-3-(4-methylene piperidin-1-yl)-1-(1H-1,2,4-triazol-1-yl)butan-2-ol, impurities and isomers of efinaconazole or salt thereof.

In one embodiment, the acid addition salt of (2R,3R)-2-(2,4-difluorophenyl)-3-(4-methylene piperidin-1-yl)-1-(1H-1,2,4-triazol-1-yl)butan-2-ol is separated from the reaction mixture containing the acid addition salt of (2R,3R)-2-(2,4-difluorophenyl)-3-(4-methylene piperidin-1-yl)-1-(1H-1,2,4-triazol-1-yl)butan-2-ol, impurities and isomers of efinaconazole or salt thereof based on their difference in solubility in the reaction mixture.

In one embodiment, the acid addition salt of (2R,3R)-2-(2,4-difluorophenyl)-3-(4-methylenepiperidin-1-yl)-1-(1H-1,2,4-triazol-1-yl)butan-2-ol is selectively separated from the from the reaction mixture containing the acid addition salt of (2R,3R)-2-(2,4-difluorophenyl)-3-(4-methylene piperidin-1-yl)-1-(1H-1,2,4-triazol-1-yl)butan-2-ol, impurities and isomers of efinaconazole or salt thereof by addition of a suitable anti-solvent.

In one embodiment, the separation is effected by the acid addition salt of (2R,3R)-2-(2,4-difluorophenyl)-3-(4-methylene piperidin-1-yl)-1-(1H-1,2,4-triazol-1-yl)butan-2-ol being soluble in a suitable solvent and the impurities and isomers of efinaconazole or salt thereof being insoluble in the solvent.

In one embodiment, the separation is effected by the acid addition salt of (2R,3R)-2-(2,4-difluorophenyl)-3-(4-methylenepiperidin-1-yl)-1-(1H-1,2,4-triazol-1-yl)butan-2-ol being insoluble in a suitable solvent and the impurities and isomers of efinaconazole or salt thereof being soluble in the solvent.

In one embodiment, the acid addition salt of (2R,3R)-2-(2,4-difluorophenyl)-3-(4-methylenepiperidin-1-yl)-1-(1H-1,2,4-triazol-1-yl)butan-2-ol is selectively separated from the reaction mixture containing the acid addition salt of (2R,3R)-2-(2,4-difluorophenyl)-3-(4-methylenepiperidin-1-yl)-1-(1H-1,2,4-triazol-1-yl)butan-2-ol, impurities and isomers of efinaconzole or salt thereof comprising:

i) removing solvent from the reaction mixture containing the acid addition salt of (2R,3R)-2-(2,4-difluorophenyl)-3-(4-methylenepiperidin-1-yl)-1-(1H-1,2,4-triazol-1-yl)butan-2-ol, impurities and isomers of efinaconazole or salt and thereof; and ii) optionally, adding a second solvent to step '(i)'.

In one embodiment, in step (i) of the above process involves partial or complete removal of the solvent from the reaction mixture containing the acid addition salt of (2R,3R)-2-(2,4-difluorophenyl)-3-(4-methylenepiperidin-1-yl)-1-(1H-1,2,4-triazol-1-yl)butan-2-ol, impurities and isomers of efinaconazole or salt thereof.

In one embodiment, the removal of solvent is carried out by methods selected from the group consisting of filtration, distillation, evaporation, centrifugation, spray drying and freeze drying.

In one embodiment, step (ii) of the above process involves optional addition of a second solvent to the reaction mixture containing acid addition salt of (2R,3R)-2-(2,4-difluorophenyl)-3-(4-methylenepiperidin-1-yl)-1-(1H-1,2,4-triazol-1-yl)butan-2-ol, impurities and isomers of efinaconazole or salt thereof.

The addition of a second solvent is carried out optionally, if the solvent is completely removed in the above step (i).

The second solvent may be selected from, but is not limited to alcohols such as methanol, ethanol, n-propanol, 2-propanol; esters such as ethyl acetate, butyl acetate, isopropyl acetate; hydrocarbons such as hexane, heptane, toluene, cyclohexane, xylene; ethers such as diethyl ether, di-isopropyl ether; ketones such as acetone, methyl ethyl ketone, methyl isobutyl ketone; water or mixtures thereof.

In one embodiment, the Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol) is separated from the reaction mixture containing Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol, impurities and the isomers of efinaconazole or salt thereof by method of filtration.

In one embodiment, the present invention provides a process for the preparation of (2R,3R)-2-(2,4-difluorophenyl)-3-(4-methylenepiperidin-1-yl)-1-(1H-1,2,4-triazol-1-yl)butan-2-ol [efinaconazole], a compound of formula I, comprising converting Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol, a compound of formula VIII to (2R,3R)-2-(2,4-difluorophenyl)-3-(4-methylenepiperidin-1-yl)-1-(1H-1,2,4-triazol-1-yl)butan-2-ol.

In one embodiment, the present invention provides a process for the preparation of (2R,3R)-2-(2,4-difluorophenyl)-3-(4-methylenepiperidin-1-yl)-1-(1H-1,2,4-triazol-1-yl)butan-2-ol [efinaconazole], a compound of formula I, comprising converting Di-toluoyl-D-tartaric salt of (2R,3R)-2-(2,4-difluorophenyl)-3-(4-methylenepiperidin-1-yl)-1-(1H-1,2,4-triazol-1-yl)butan-2-ol, a compound of formula VII to (2R,3R)-2-(2,4-difluorophenyl)-3-(4-methylenepiperidin-1-yl)-1-(1H-1,2,4-triazol-1-yl)butan-2-ol.

The Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol) obtained may be optionally purified or recrystallized in a solvent.

In one embodiment, the purification or recrystallization may be carried out in a suitable solvent selected from alcohols such as methanol, ethanol, propanol, isopropanol and the like; esters such as ethyl acetate, isopropyl acetate and the like; ketone such as acetone, methyl ethyl ketone, methyl isobutyl ketone and the like, water or mixtures thereof.

In one embodiment, the Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol) is recrystallized from a mixture of ethanol and water.

In one embodiment, step 'd' of the above process involves converting the acid addition salt of (2R,3R)-2-(2,4-difluorophenyl)-3-(4-methylene piperidin-1-yl)-1-(1H-1,2,4-triazol-1-yl)butan-2-ol to (2R,3R)-2-(2,4-difluorophenyl)-3-(4-methylene piperidin-1-yl)-1-(1H-1,2,4-triazol-1-yl)butan-2-ol.

In one embodiment, the acid addition salt of (2R,3R)-2-(2,4-difluorophenyl)-3-(4-methylene piperidin-1-yl)-1-(1H-1,2,4-triazol-1-yl)butan-2-ol is subjected to basification to obtain (2R,3R)-2-(2,4-difluorophenyl)-3-(4-methylene piperidin-1-yl)-1-(1H-1,2,4-triazol-1-yl)butan-2-ol.

Base may be selected from the group consisting of organic or inorganic base. Inorganic bases may be selected from the group consisting of hydroxides such as sodium hydroxide, potassium hydroxide, calcium hydroxide, lithium hydroxide; carbonate such as of sodium carbonate, potassium carbonate, calcium carbonate, lithium carbonate; alkoxide such as sodium methoxide, potassium methoxide; bicarbonates such as sodium bicarbonate, potassium bicarbonate, lithium bicarbonate; ammonia and the like. Organic bases may be selected from the group consisting of organic amines such as triethylamine, diisopropylethylamine, N, N-dimethylaniline, pyridine and the like.

In one embodiment, (2R,3R)-2-(2,4-difluorophenyl)-3-(4-methylene piperidin-1-yl)-1-(1H-1,2,4-triazol-1-yl)butan-2-ol is isolated by methods known in the art such as extraction, centrifugation, filtration and the like.

In one embodiment, in step 'd' of the above process the D-di-toluoyl tartaric acid salt of (2R,3R)-2-(2,4-difluorophenyl)-3-(4-methylenepiperidin-1-yl)-1-(1H-1,2,4-triazol-1-yl)butan-2-ol or L-di-toluoyl tartaric acid salt of (2R,3R)-2-(2,4-difluorophenyl)-3-(4-methylenepiperidin-1-yl)-1-(1H-1,2,4-triazol-1-yl)butan-2-ol is converted to (2R,3R)-2-(2,4-difluorophenyl)-3-(4-methylenepiperidin-1-yl)-1-(1H-1,2,4-triazol-1-yl)butan-2-ol by treating with potassium carbonate. The (2R,3R)-2-(2,4-difluorophenyl)-3-(4-methylenepiperidin-1-yl)-1-(1H-1,2,4-triazol-1-yl) butan-2-ol thus obtained is isolated by extracting from the reaction mixture using a suitable solvent.

Solvent may be selected from the group consisting of chlorinated solvents such as methylene dichloride, ethylene dichloride, chloroform, carbon tetrachloride; ethers such as diethyl ether, methyl tertiary butyl ether, di-isopropyl ether, tetrahydrofuran; nitriles such as acetonitrile, propionitrile; esters such as ethyl acetate, butyl acetate, isopropyl acetate; hydrocarbons such as, cyclohexane, toluene, xylene, hexane; alcohols such as methanol, ethanol, butanol, isopropanol, n-propanol; sulfoxides such as dimethyl sulfoxide; amides such as dimethyl formamide, dimethyl acetamide; ketones such as acetone, methyl ethyl ketone, methyl isobutyl ketone; water and or mixtures thereof.

In one embodiment, the present invention provides a process for the preparation of (2R,3R)-2-(2,4-difluorophenyl)-3-(4-methylenepiperidin-1-yl)-1-(1H-1,2,4-triazol-1-yl)butan-2-ol [efinaconazole], a compound of formula I comprising:

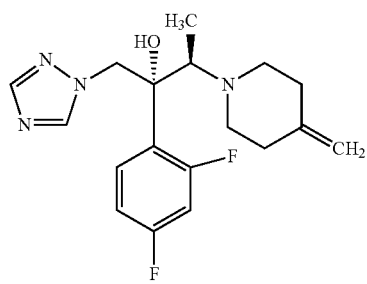

I a) reacting (2R,3 S)-2-(2,4-difluorophenyl)-3-methyl-2-[(1H-1,2,4-triazol-1-yl) methyl]oxirane, a compound of formula II, with 4-methylenepiperidine, a compound of formula III or salt thereof, in the presence of a lewis acid to obtain crude efinaconazole;

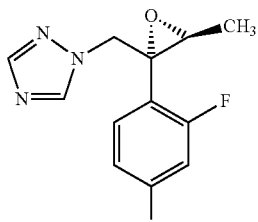

II

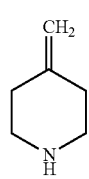

III b) reacting the crude efinaconazole obtained from step 'a' with an acid selected from the group consisting of an inorganic acid, an organic carboxylic acid and an optically active acid to obtain a reaction mixture containing an acid addition salt of (2R,3R)-2-(2,4-difluorophenyl)-3-(4-methylene piperidin-1-yl)-1-(1H-1,2,4-triazol-1-yl)butan-2-ol;

c) separating the acid addition salt of (2R,3R)-2-(2,4-difluorophenyl)-3-(4-methylene piperidin-1-yl)-1-(1H-1,2,4-triazol-1-yl)butan-2-ol from the reaction mixture; and d) converting the acid addition salt of (2R,3R)-2-(2,4-difluorophenyl)-3-(4-methylene piperidin-1-yl)-1-(1H-1,2,4-triazol-1-yl)butan-2-ol) to (2R,3R)-2-(2,4-difluorophenyl)-3-(4-methylene piperidin-1-yl)-1-(1H-1,2,4-triazol-1-yl)butan-2-ol.

In one embodiment, the present invention provides Di-toluoyl-D-tartaric acid salt of (2R,3R)-2-(2,4-difluorophenyl)-3-(4-methylene piperidin-1-yl)-1-(1H-1,2,4-triazol-1-yl)butan-2-ol, compound of formula VII or Di-toluoyl-L-tartaric acid salt of (2R,3R)-2-(2,4-difluorophenyl)-3-(4-methylene piperidin-1-yl)-1-(1H-1,2,4-triazol-1-yl)butan-2-ol, a compound of formula VIII.

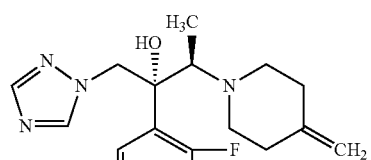

VII

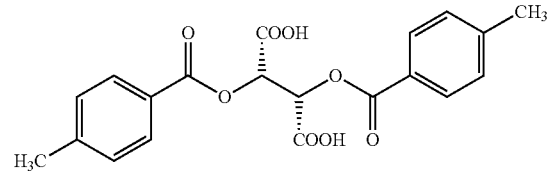

-continued

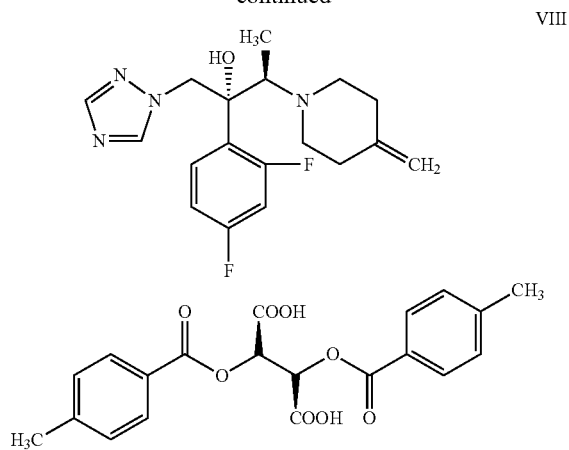

VIII

In one embodiment, the present invention provides a process for the preparation of D-di-toluoyl tartaric acid salt of (2R,3R)-2-(2,4-difluorophenyl)-3-(4-methylene piperidin-1-yl)-1-(1H-1,2,4-triazol-1-yl)butan-2-ol or L-di-toluoyl tartaric acid salt of (2R,3R)-2-(2,4-difluorophenyl)-3-(4-methylene piperidin-1-yl)-1-(1H-1,2,4-triazol-1-yl)butan-2-ol comprising reacting the crude efinaconazole with D-di-toluoyl tartaric acid, or with L-di-toluoyl tartaric acid to obtain D-di-toluoyl tartaric acid salt of (2R,3R)-2-(2,4-difluorophenyl)-3-(4-methylenepiperidin-1-yl)-1-(1H-1,2,4-triazol-1-yl)butan-2-ol, a compound of formula VII or L-di-toluoyl tartaric acid salt of (2R,3R)-2-(2,4-difluorophenyl)-3-(4-methylenepiperidin-1-yl)-1-(1H-1,2,4-triazol-1-yl)butan-2-ol, a compound of formula VIII.

In one embodiment, the present invention provides a process for the preparation of D or L di-toluoyl tartaric acid salt of (2R,3R)-2-(2,4-difluorophenyl)-3-(4-methylene piperidin-1-yl)-1-(1H-1,2,4-triazol-1-yl)butan-2-ol comprising reacting the crude efinaconazole with a solution of D-di-toluoyl tartaric acid or L-di-toluoyl tartaric acid in a solvent to obtain D-di-toluoyl tartaric acid salt of (2R,3R)-2-(2,4-difluorophenyl)-3-(4-methylenepiperidin-1-yl)-1-(1H-1,2,4-triazol-1-yl)butan-2-ol or L-di-toluoyl tartaric acid salt of (2R,3R)-2-(2,4-difluorophenyl)-3-(4-methylenepiperidin-1-yl)-1-(1H-1,2,4-triazol-1-yl)butan-2-ol.

In one embodiment, crude efinaconazole may be purified in a suitable solvent prior to the reaction with an acid to form the acid addition salt thereof.

In one embodiment, crude efinaconazole is reacted with Di-toluoyl-L-tartaric acid to obtain Di-toluoyl-L-tartaric acid salt of (2R,3R)-2-(2,4-difluorophenyl)-3-(4-methylene piperidin-1-yl)-1-(1H-1,2,4-triazol-1-yl)butan-2-ol.

In one embodiment, D-di-toluoyl tartaric acid salt of (2R,3R)-2-(2,4-difluorophenyl)-3-(4-methylene piperidin-1-yl)-1-(1H-1,2,4-triazol-1-yl)butan-2-ol or L-di-toluoyl tartaric acid salt of (2R,3R)-2-(2,4-difluorophenyl)-3-(4-methylenepiperidin-1-yl)-1-(1H-1,2,4-triazol-1-yl)butan-2-ol may be purified in a solvent.

In one embodiment, the present invention provides a process for the preparation of crystalline (2R,3R)-2-(2,4-difluorophenyl)-3-(4-methylene piperidin-1-yl)-1-(1H-1,2,4-triazol-1-yl)butan-2-ol, the compound of formula I comprising:
i) treating (2R,3R)-2-(2,4-difluorophenyl)-3-(4-methylene piperidin-1-yl)-1-(1H-1,2,4-triazol-1-yl)butan-2-ol, with a solvent to obtain a reaction mixture;
ii) optionally adding an anti-solvent; and
iii) isolating (2R,3R)-2-(2,4-difluorophenyl)-3-(4-methylene piperidin-1-yl)-1-(1H-1,2,4-triazol-1-yl)butan-2-ol from the above step i) or step ii)
wherein the solvent is selected from the group consisting of C1-C5 alcohol, nitrile, water, sulfoxides, hydrocarbons, esters, ethers, amides, chlorinated hydrocarbon and mixtures thereof.

In one embodiment, the step i) of the above process involves treating ((2R,3R)-2-(2,4-difluorophenyl)-3-(4-methylenepiperidin-1-yl)-1-(1H-1,2,4-triazol-1-yl)butan-2-ol), with a solvent to obtain a reaction mixture.

The solvent C1-C5 alcohol may be selected from the group consisting of methanol, ethanol, butanol, isopropanol, n-propanol; nitriles may be selected from the group consisting acetonitrile, propionitrile; water; sulfoxides such as dimethyl sulfoxide; hydrocarbons such as, cyclohexane, toluene, xylene, hexane; esters such as ethyl acetate, butyl acetate, isopropyl acetate; ethers such as diethyl ether, methyl tertiary butyl ether, di-isopropyl ether, tetrahydrofuran; amides such as dimethyl formamide, dimethyl acetamide; chlorinated hydrocarbons such as methylene dichloride, ethylene dichloride, chloroform, carbon tetrachloride; and or mixtures thereof.

In one embodiment, in step ii) of the above process an anti-solvent is added to the reaction mixture of (2R,3R)-2-(2,4-difluorophenyl)-3-(4-methylenepiperidin-1-yl)-1-(1H-1,2,4-triazol-1-yl)butan-2-ol in a solvent.

The anti-solvent may be selected from the group consisting of water, hydrocarbons such as, cyclohexane, toluene, xylene, hexane; alcohols such as methanol, ethanol, butanol, isopropanol, n-propanol.

In one embodiment, in step 'iii)' of the above process (2R,3R)-2-(2,4-difluorophenyl)-3-(4-methylenepiperidin-1-yl)-1-(1H-1,2,4-triazol-1-yl)butan-2-ol is isolated from the reaction mixture of step i) or step ii) by methods known in the art such as extraction, filtration, centrifugation and the like.

In one embodiment, the present invention provides crystalline salt of (2R,3R)-2-(2,4-difluorophenyl)-3-(4-methylenepiperidin-1-yl)-1-(1H-1,2,4-triazol-1-yl)butan-2-ol.

In one embodiment, the present invention provides crystalline D-di-toluoyl-tartaric salt of (2R,3R)-2-(2,4-difluorophenyl)-3-(4-methylenepiperidin-1-yl)-1-(1H-1,2,4-triazol-1-yl)butan-2-ol or L-di-toluoyl-tartaric salt of (2R,3R)-2-(2,4-difluorophenyl)-3-(4-methylenepiperidin-1-yl)-1-(1H-1,2,4-triazol-1-yl)butan-2-ol.

In one embodiment, the present invention provides crystalline L-di-toluoyl-tartaric salt of (2R,3R)-2-(2,4-difluorophenyl)-3-(4-methylenepiperidin-1-yl)-1-(1H-1,2,4-triazol-1-yl)butan-2-ol.

Figure 2:
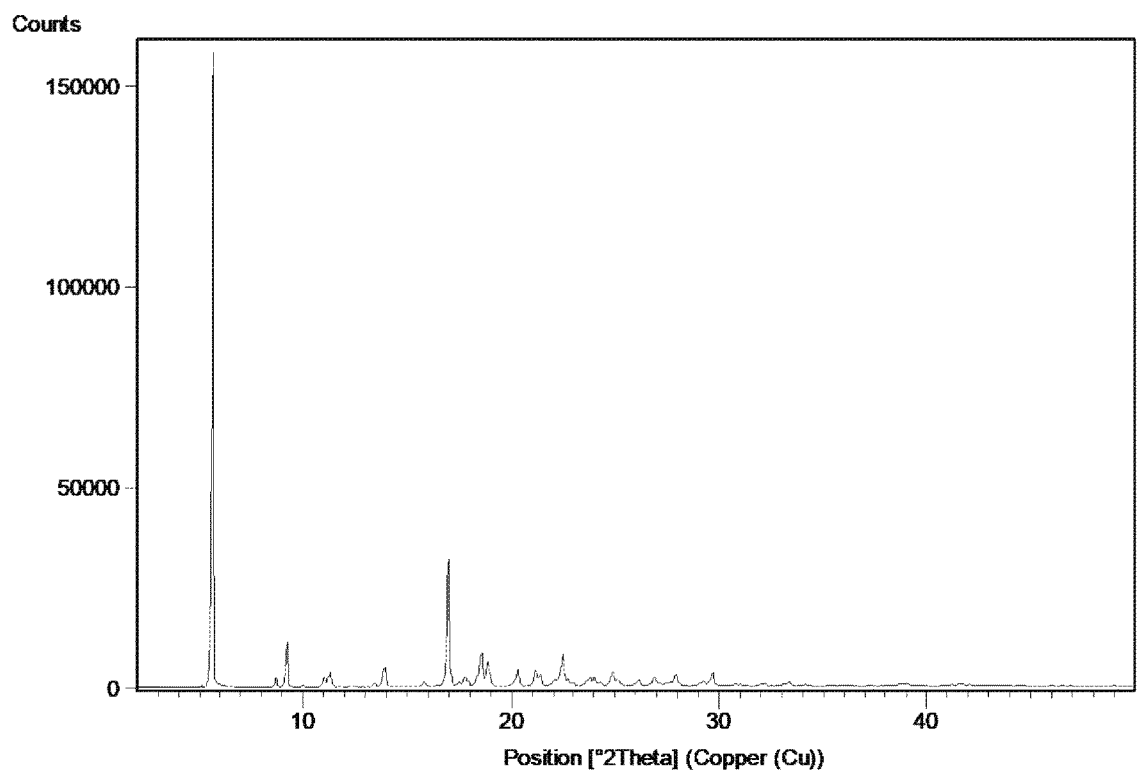

In one embodiment, the present invention provides crystalline Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol characterized by X-ray diffraction (XRD) spectrum which is substantially in accordance with FIG. 2.

In one embodiment, the present invention provides crystalline Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol characterized by X-ray Diffraction (XRD) spectrum having peak reflections at 5.6, 9.2, 13.9, 16.9 and 18.6±0.2 degrees 2 theta.

In one embodiment, the present invention provides crystalline Di-toluoyl-L-tartaric salt of (2R,3R)-2-(2,4-difluorophenyl)-3-(4-methylenepiperidin-1-yl)-1-(1H-1,2,4-triazol-1-yl)butan-2-ol characterized by 1HNMR having peaks at 0.751, 0.772, 2.248, 2.401, 2.459, 2.851, 2.867, 2.885, 3.163, 3.186, 4.636, 4.790, 4.839, 4.868, 4.915, 5.829, 6.887, 6.916, 6.936, 7.079, 7.111, 7.142, 7.300, 7.329, 7.355, 7.381, 7.407, 7.683, 7.893, 7.919, and 8.311 (300 MHz, DMSO d$_6$).

In one embodiment, the present invention provides crystalline Di-toluoyl-D-tartaric salt of (2R,3R)-2-(2,4-difluorophenyl)-3-(4-methylenepiperidin-1-yl)-1-(1H-1,2,4-triazol-1-yl)butan-2-ol.

In one embodiment, the present invention provides use of a salt of (2R,3R)-2-(2,4-difluorophenyl)-3-(4-methylene piperidin-1-yl)-1-(1H-1,2,4-triazol-1-yl)butan-2-ol for obtaining (2R,3R)-2-(2,4-difluorophenyl)-3-(4-methylene piperidin-1-yl)-1-(1H-1,2,4-triazol-1-yl)butan-2-ol wherein content of (2S,3 S) isomer of efinaconazole, compound of formula IV and/or (2R,3 S) isomer of efinaconazole, compound of formula V and/or (2S,3R) isomer of efinaconazole compound of formula VI is less than 0.5% w/w with respect to (2R,3R)-2-(2,4-difluorophenyl)-3-(4-methylene piperidin-1-yl)-1-(1H-1,2,4-triazol-1-yl)butan-2-ol as determined by HPLC.

In one embodiment, the present invention provides (2R, 3R)-2-(2,4-difluorophenyl)-3-(4-methylene piperidin-1-yl)-1-(1H-1,2,4-triazol-1-yl)butan-2-ol, a compound of formula I

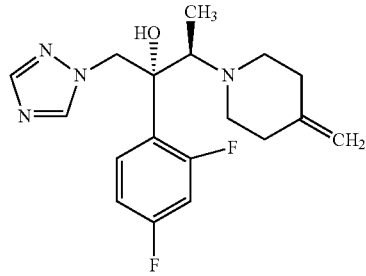

wherein content of (2S,3 S) isomer of efinaconazole, compound of formula IV and/or (2R,3 S) isomer of efinaconazole, compound of formula V and/or (2S,3R) isomer of efinaconazole, compound of formula VI is less than 0.5% w/w with respect to (2R,3R)-2-(2,4-difluorophenyl)-3-(4-methylene piperidin-1-yl)-1-(1H-1,2,4-triazol-1-yl)butan-2-ol as determined by HPLC.

In one embodiment, the present invention provides a process for the preparation of (2R,3R)-2 (2,4-difluorophenyl)-3-(4-methylene piperidin-1-yl)-1-(1H-1,2,4-triazol-1l-yl) butan-2-ol, the compound of formula I.

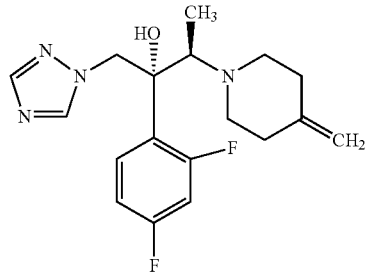

comprising reacting (2R,3S)-2-(2,4-difluorophenyl)-3-methyl-2-[(1H-1,2,4-triazol-1-yl)methyl]oxirane, a compound of formula II, with 4-methylenepiperidine, a compound of formula III or salt thereof in the presence of a Lewis acid.

In one embodiment, the compound of formula II is reacted with the compound of formula III in the presence of a lewis acid at a temperature of about 15° C. to reflux temperature of the solvent. Preferably, the reaction transpires at a temperature of about 50° C. to about reflux temperature of the solvent.

In one embodiment, the present invention provides a process for the preparation of ((2R,3R)-2 (2,4-difluorophenyl)-3-(4-methylene piperidin-1-yl)-1-(1H-1,2,4-triazol-1l-yl) butan-2-ol, the compound of formula I

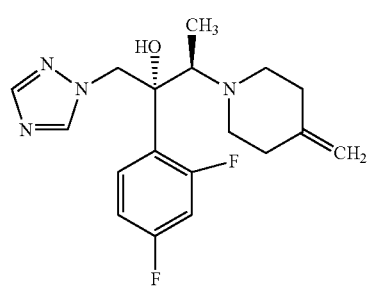

comprising reacting (2R,3S)-2-(2,4-difluorophenyl)-3-methyl-2-[(1H-1,2,4-triazol-1-yl)methyl]oxirane, a compound of formula II, with 4-methylenepiperidine, a compound of formula III or salt thereof in the presence of a lewis acid and a phase transfer catalyst.

In one embodiment, (2R,3R)-2-(2,4-difluorophenyl)-3-(4-methylenepiperidin-1-yl)-1-(1H-1,2,4-triazol-1-yl)butan-2-ol is crystallized from a mixture of aqueous alcohol obtain crystalline efinaconazole.

In one embodiment, (2R,3R)-2-(2,4-difluorophenyl)-3-(4-methylenepiperidin-1-yl)-1-(1H-1,2,4-triazol-1-yl)butan-2-ol is crystallized from a mixture of aqueous alcohol obtain crystalline efinaconazole wherein the ratio of alcohol to water is 6:4 or 7:3.

The alcohol may be selected from the group consisting of C1-C5 alcohol such as methanol, ethanol, propanol, isobutanol, isopropanol and the like.

In one embodiment, (2R,3R)-2-(2,4-difluorophenyl)-3-(4-methylenepiperidin-1-yl)-1-(1H-1,2,4-triazol-1-yl)butan-2-ol is crystallized from a mixture of ethanol and water to obtain crystalline efinaconazole.

In one embodiment, the present invention provides crystalline efinaconazole characterized by X-ray diffraction (XRD) spectrum having peak reflections at about 7.6, 14.9, 15.3, 16.6 and 18.8±0.2 degrees 2 theta.

In one embodiment, the present invention provides crystalline efinaconazole characterized by X-ray diffraction (XRD) spectrum having peak reflections at about 7.6, 14.9, 15.3, 16.6 and 18.8±0.2 degrees 2 theta, which is substantially in accordance with FIG. 1.

In one embodiment, the present invention provides efinaconazole wherein the content of (2S,3S) isomer of efinaconazole, compound of formula IV is less than 0.5% w/w with respect to efinaconazole as determined by HPLC.

In one embodiment, the present invention provides efinaconazole wherein the content of (2R,3S) isomer of efinaconazole compound of formula V is less than 0.5% w/w with respect to efinaconazole as determined by HPLC.

In one embodiment, the present invention provides efinaconazole wherein the content of (2S,3R) isomer of efinaconazole, compound of formula VI is less than 0.5% w/w with respect to efinaconazole as determined by HPLC.

In one embodiment, the present invention provides amorphous (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides an alcohol solvate of (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides a methanol solvate of (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides a ethanol solvate of (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides a isopropanol solvate of (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides a hydrate of (2R,3R)-2-(2,4-difluorophenyl)-3-(4-methylene piperidin-1-yl)-1-(1H-1,2,4-triazol-1-yl)butan-2-ol, a compound of formula I.

In one embodiment, the present invention provides (2R,3R)-2-(2,4-difluorophenyl)-3-(4-methylene piperidin-1-yl)-1-(1H-1,2,4-triazol-1-yl)butan-2-ol, a compound of formula I with a chemical purity of at least 99% w/w and a chiral purity of at least 99% w/w as determined by HPLC.

In one embodiment, the present invention provides pharmaceutical compositions comprising efinaconazole or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns.

In one embodiment, the present invention provides efinaconazole or salt obtained by the processes herein described having D90 particle size of less than about 16 microns and D50 particle size of less than about 8 microns.

The particle size disclosed here can be obtained by, for example, any milling, grinding, micronizing or other particle size reduction method known in the art to bring the solid state efinaconazole or salt into any of the foregoing desired particle size range.

In one embodiment, the present invention provides a method for preparing efinaconazole, or salt thereof, suitable for pharmaceutical use, comprising the steps of:
a) providing a batch of efinaconazole or a salt thereof;
b) assessing the purity of said batch of efinaconazole or salt thereof, by using at least one compound selected from the group consisting of IX, X, II, V and VI as a reference marker to determine the level of the reference marker compound; and
c) selecting the batch of efinaconazole only if the percentage of the reference marker compound is less than 0.15% w/w as determined by HPLC

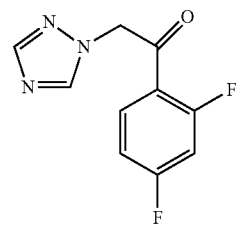

X

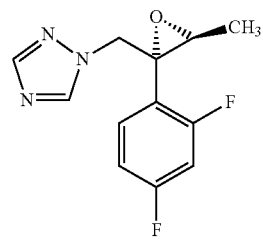

II

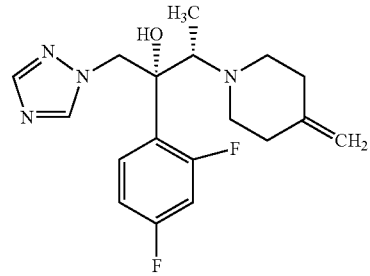

V

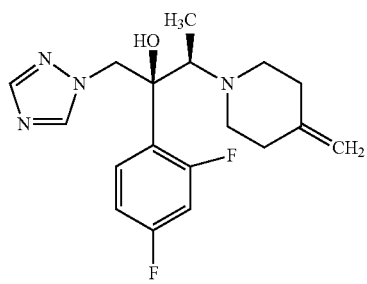

VI wherein in compound IX when i) R is 2,4-difluoro, G is selected from the group consisting of hydroxy, 4-methylenepiperidine-N-oxide and amino; ii) when G is 4-methylenepiperidine, R is selected from the group consisting of 4-fluoro and H.

In one embodiment, the compound of formula IX is a compound as shown below below,

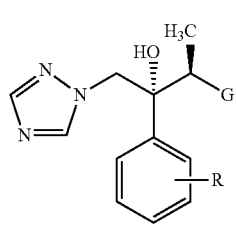

IX

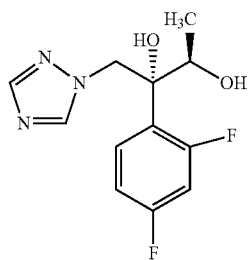

XI

XII

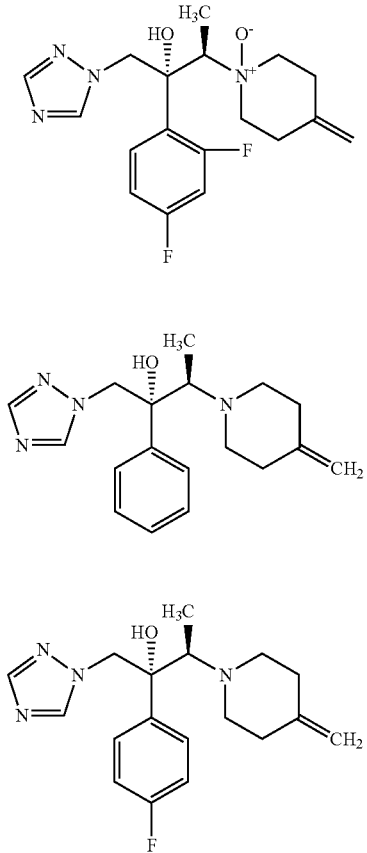

XIII

XIV

In one embodiment, the present invention provides a method of assessing the purity of efinaconazole and pharmaceutical compositions thereof comprising the steps of:

a) providing a standard solution of at least one of the reference marker compound selected from the group consisting of IX, X, II, V and VI

IX

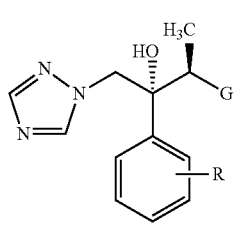

X

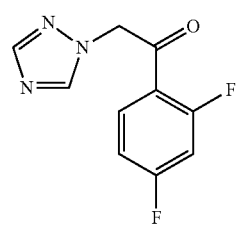

II

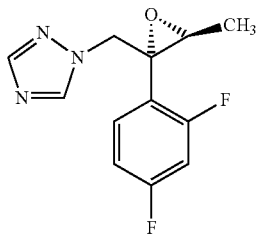

V

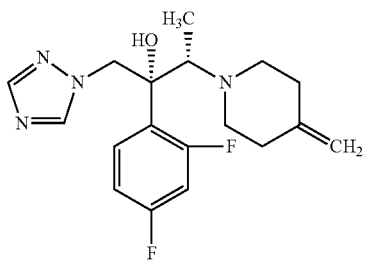

VI

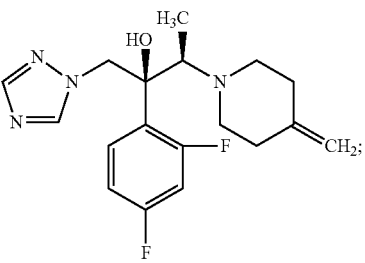

and
(b) using the solution as a reference marker to determine the level of the reference marker compound.

In one embodiment, the present invention provides a compound of formula XII

XII

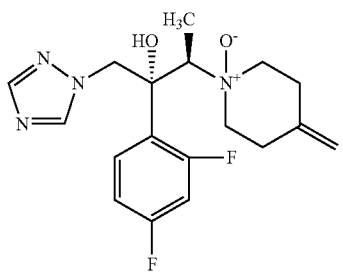

by 1HNMR having peaks at 1.38, 2.03-2.14, 2.49, 2.78, 2.96, 3.18-3.58, 3.75, 4.64-5.03, 7.01, 7.22, 7.63, 7.73, and 8.33 (300 MHz, DMSO $d_6$).

In one embodiment, efinaconazole, the compound of formula XII is prepared by reacting efinaconazole with m-perchlorobenzoic acid.

The present invention provides efinaconazole as characterized and analyzed by following techniques:

A]: Instrumental settings for HPLC for chemical purity: Reagents and Solvents Potassium dihydrogen phosphate, Potassium hydroxide, Acetonitrile, Water Column: Inertsil ODS 3V, 250×4.6 mm, 5μ Column temperature: 30° C. Mobile Phase A: Buffer: Acetonitrile Mobile Phase B: Acetonitrile Diluent: Water:Acetonitrile (40:60, v/v) Flow Rate: 1.0 mL/minute Detection: UV 210 nm Injection Volume: 20 μL.

B] Instrumental settings for HPLC for chiral purity Reagents and Solvents: n-Hexane (HPLC Grade, Rankem) Ethanol (HPLC Grade) Diethyl amine (Merck) Column: Chiralcel OD-H, 250×4.6 mm, 5µ Column temperature: 30° C. Mobile Phase: n-Hexane:Ethanol:Diethyl amine (96:04:0.02, v/v/v) Diluent: n-Hexane:Ethanol (90:10, v/v) Flow Rate: 1.0 mL/minute Detection: UV 210 nm Injection Volume: 20 µL Run time: 60 minutes.

C] Instrumental settings for NMR: Proton NMR spectra were recorded in DMSO-$d_6$ using NMR instrument-Varian 300 MHZ.

D] X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator [1]; Scanning Mode; Active length (2Theta)=2.122°; generator 45 KV; tube current 40 mAmp. The samples were scanned in the full 2θ range of 2-50° with a "time-per-step" 50 seconds.

E] PSD: Particle size analysis was performed on Malvern Mastersizer 2000.

The examples that follow are provided to enable one skilled in the art to practice the invention and are merely illustrative of the invention. The examples should not be read as limiting the scope of the invention as defined in the features and advantages.

EXAMPLES

Example 1: Preparation of (2R,3R)-2-(2,4-Difluorophenyl)-3-(4-methylene-1-piperidinyl)-1-(1H-1,2,4-triazol-1-yl)-2-butanol To a suspension of 4-methylene-piperidine hydrochloride (1.59 gm) in ethanol (2.5 ml), lithium carbonate (1.47 gm) was added at about 25-30° C. To this reaction mixture aqueous lithium bromide (0.84 gm) was added and the reaction mass was stirred. To this 1-{[2-(2,4-dimethylphenyl)oxiran-2-yl]methyl}-1H-1,2,4-triazole (0.5 gm) was added and heated to reflux for about 72 hrs. On completion, the reaction mass was concentrated under vacuum and the residue was taken up in a mixture of ethyl acetate and water. The layers were separated. The ethyl acetate layer was concentrated under vacuum. The residue was stirred in n-heptane (1.5 ml) and at about 5-10° C. The precipitated solid was filtered and dried under vacuum to obtain (2R,3R)-2-(2,4-Difluorophenyl)-3-(4-methylene-1-piperidinyl)-1-(1H-1,2,4-triazol-1-yl)-2-butanol.

Example 2: Preparation of (2R,3R)-2-(2,4-Difluorophenyl)-3-(4-methylene-1-piperidinyl)-1-(1H-1,2,4-triazol-1-yl)-2-butanol The experiment 1 was repeated in water as a solvent instead of ethanol.

Example 3: Preparation of (2R,3R)-2-(2,4-Difluorophenyl)-3-(4-methylene-1-piperidinyl)-1-(1H-1,2,4-triazol-1-yl)-2-butanol The experiment 1 was repeated with potassium carbonate as a base instead of lithium carbonate.

Example 4: Preparation of (2R,3R)-2-(2,4-Difluorophenyl)-3-(4-methylene-1-piperidinyl)-1-(1H-1,2,4-triazol-1-yl)-2-butanol To a suspension of 4-methylene-piperidine hydrochloride (1.59 gm) in dichloromethane (15 ml), powdered potassium hydroxide (0.66 gm) were added and stirred. The reaction mixture was filtered. The filtrate was concentrated under vacuum to obtain oil. To the obtained oil methanol (2.5 ml) was added followed by addition of lithium carbonate (1.47 gm) and aqueous lithium bromide (0.84 gm) solution to obtain a reaction mixture. To this reaction mixture 1-{[2-(2,4-dimethylphenyl)oxiran-2-yl]methyl}-1H-1,2,4-triazole (0.5 gm) was added and heated to reflux. On completion of the reaction, the reaction mass was concentrated under vacuum to obtain a residue. The residue was treated with a mixture of ethyl acetate (5 ml) and water (5 ml). The layers were separated and ethyl acetate layer was concentrated under vacuum. The obtained residue was taken in n-heptane and stirred for about 3 hrs at about 5-10° C. The precipitated solid was filtered and dried under vacuum to obtain (2R,3R)-2-(2,4-Difluorophenyl)-3-(4-methylene-1-piperidinyl)-1-(1H-1,2,4-triazol-1-yl)-2-butanol.

Example 5: Preparation of (2R,3R)-2-(2,4-Difluorophenyl)-3-(4-methylene-1-piperidinyl)-1-(1H-1,2,4-triazol-1-yl)-2-butanol To a suspension of 4-methylene-piperidine hydrochloride (0.79 gm) in dichloromethane (15 ml), powdered potassium hydroxide (0.55 gm) and water (10 ml) were added. The reaction mixture was stirred and the layers were separated. The organic layer was concentrated under vacuum at about 40° C. to afford an oil. The oil dissolved in acetonitrile followed by addition of lithium bromide (0.519 gm) and 1-{[2-(2,4-dimethylphenyl)oxiran-2-yl]methyl}-1H-1,2,4-triazole (0.5 gm) at about 25° C. The reaction mass was heated to reflux. On completion of the reaction, the reaction mass was concentrated under vacuum. The residue obtained was taken in ethyl acetate and water and stirred for about 30 min. The layers were separated and ethyl acetate layer was concentrated under vacuum. The obtained residue was taken in n-heptane and stirred for about 3 hrs at about 5-10° C. The precipitated solid was filtered and dried under vacuum to obtain 0.4 gm (2R,3R)-2-(2,4-Difluorophenyl)-3-(4-methylene-1-piperidinyl)-1-(1H-1,2,4-triazol-1-yl)-2-butanol.

Example 6a: Preparation of L-di-toluoyl-tartaric acid salt of (2R,3R)-2-(2,4-Difluorophenyl)-3-(4-methylene-1-piperidinyl)-1-(1H-1,2,4-triazol-1-yl)-2-butanol Powdered potassium hydroxide (5.5 gm) was added to a suspension of 4-methylene-piperidine hydrochloride (7.9 gm) in dichloromethane (80 ml) and stirred. The reaction mixture was filtered and the filtrate was concentrated under vacuum at about 35°–40° C. The obtained oil was dissolved in toluene (100 ml) followed by addition of lithium bromide (5.19 gm), 1-{[2-(2,4-dimethylphenyl)oxiran-2-yl]methyl}-1H-1,2,4-triazole (5 gm) and tetrabutylammonium bromide (0.5 gm). The reaction mass was heated to 85° C. for 15-20 hrs. On completion of the reaction, the reaction mass was cooled to 25-30° C. To this reaction mixture water was added and the layers were separated. The toluene layer was concentrated under vacuum to obtain residue. To this residue a solution of Di-p-toluoyl-L-tartaric acid (9.98 gm) in ethanol was added at 70° C. The reaction mixture was stirred and then cooled to 20-25° C. and again stirred for 3 Hrs. The precipitated solid was filtered. This solid was taken in a mixture of ethanol:water (7:3) and heated to 75° C. to get clear solution. The reaction mixture was cooled to 20-25° C. and stirred for 3 Hrs. The precipitated solid was filtered and dried.

XRD of L-di-toluoyl tartaric acid salt of 2R,3R)-2-(2,4-Difluorophenyl)-3-(4-methylene-1-piperidinyl)-1-(1H-1,2,4-triazol-1-yl)-2-butanol

| Pos. [°2Th.] | d-spacing [Å] | Rel. Int. [%] |
|---|---|---|
| 3.57 | 24.74 | 0.04 |
| 5.09 | 17.35 | 0.41 |
| 5.64 | 15.65 | 100.00 |
| 8.72 | 10.13 | 1.18 |
| 9.24 | 9.56 | 4.70 |
| 9.98 | 8.85 | 0.26 |
| 11.03 | 8.01 | 1.18 |
| 11.29 | 7.83 | 2.22 |
| 11.81 | 7.40 | 0.12 |
| 12.39 | 7.14 | 0.16 |
| 13.46 | 6.57 | 0.45 |
| 13.91 | 6.36 | 2.44 |
| 15.30 | 5.78 | 0.10 |
| 15.78 | 5.61 | 0.49 |
| 16.97 | 5.22 | 19.08 |
| 17.49 | 5.06 | 0.50 |
| 17.79 | 4.98 | 1.02 |
| 17.94 | 4.94 | 0.66 |
| 18.34 | 4.83 | 0.93 |
| 18.6 | 4.77 | 3.49 |
| 18.88 | 4.69 | 2.89 |
| 20.33 | 4.36 | 1.56 |
| 21.14 | 4.20 | 2.25 |
| 21.39 | 4.15 | 1.43 |
| 22.06 | 4.02 | 0.65 |
| 22.50 | 3.95 | 2.94 |
| 22.70 | 3.91 | 0.71 |
| 23.04 | 3.855 | 0.35 |
| 23.79 | 3.73 | 0.74 |
| 24.00 | 3.70 | 0.86 |
| 24.32 | 3.65 | 0.50 |
| 24.90 | 3.57 | 1.75 |
| 25.13 | 3.54 | 0.71 |
| 26.14 | 3.40 | 0.58 |
| 26.89 | 3.31 | 0.89 |
| 27.13 | 3.28 | 0.32 |
| 27.44 | 3.25 | 0.32 |
| 27.91 | 3.19 | 1.26 |
| 28.38 | 3.14 | 0.14 |
| 29.24 | 3.053 | 0.48 |
| 29.67 | 3.01 | 1.20 |
| 30.30 | 2.94 | 0.13 |
| 30.78 | 2.90 | 0.21 |
| 32.15 | 2.78 | 0.25 |
| 33.35 | 2.68 | 0.67 |
| 34.09 | 2.62 | 0.18 |
| 34.32 | 2.61 | 0.18 |
| 34.77 | 2.57 | 0.07 |
| 35.30 | 2.54 | 0.10 |
| 35.82 | 2.50 | 0.13 |

XRD: 2R,3R)-2-(2,4-Difluorophenyl)-3-(4-methylene-1-piperidinyl)-1-(1H-1,2,4-triazol-1-yl)-2-butanol

| Pos. [°2Th.] | d-spacing [Å] | Rel. Int. [%] |
|---|---|---|
| 7.62 | 11.59 | 17.21 |
| 9.96 | 8.88 | 4.53 |
| 10.51 | 8.41 | 11.18 |
| 11.32 | 7.81 | 1.65 |
| 12.01 | 7.36 | 2.69 |
| 12.43 | 7.11 | 11.58 |
| 12.84 | 6.89 | 3.71 |
| 13.68 | 6.47 | 1.5 |
| 14.97 | 5.91 | 17.62 |
| 15.3 | 5.77 | 100.00 |
| 16.64 | 5.32 | 84.43 |
| 17.04 | 5.20 | 4.04 |
| 17.66 | 5.02 | 1.82 |
| 18.83 | 4.71 | 51.81 |
| 20.11 | 4.41 | 10.10 |
| 20.77 | 4.27 | 3.83 |
| 21.13 | 4.2 | 3.46 |
| 22.68 | 3.91 | 2.97 |
| 23.34 | 3.8 | 12.28 |
| 23.7 | 3.75 | 12.46 |
| 24.4 | 3.64 | 8.67 |
| 25.27 | 3.52 | 5.51 |
| 25.95 | 3.43 | 12.74 |
| 26.22 | 3.39 | 5.07 |
| 27.17 | 3.28 | 6.88 |
| 27.68 | 3.22 | 2.14 |
| 28.07 | 3.17 | 2.72 |
| 29.9 | 2.98 | 5.58 |
| 30.04 | 2.97 | 6.46 |
| 30.79 | 2.9 | 2.24 |
| 31.74 | 2.81 | 3.77 |
| 32.84 | 2.72 | 2.27 |
| 33.53 | 2.67 | 3.11 |
| 33.78 | 2.65 | 3.27 |
| 34.47 | 2.6 | 1.21 |
| 36.00 | 2.49 | 1.85 |
| 36.86 | 2.43 | 2.7 |
| 38.68 | 2.32 | 0.30 |
| 40.21 | 2.24 | 1.54 |
| 40.94 | 2.2 | 1.04 |
| 41.88 | 2.15 | 0.64 |
| 43.27 | 2.09 | 0.57 |
| 45.79 | 1.98 | 1.13 |
| 46.62 | 1.94 | 0.75 |
| 47.89 | 1.89 | 0.96 |

Example 6b) Preparation of (2R,3R)-2-(2,4-Difluorophenyl)-3-(4-methylene-1-piperidinyl)-1-(1H-1,2,4-triazol-1-yl)-2-butanol The solid obtained in example 6a) was taken in a dichloromethane and an aqueous solution of potassium carbonate was added to basify to a pH of 8-9. The layers were separated. The aqueous layer was extracted with methylene dichloride. The methylene dichloride layer was washed with water and concentrated under vacuum. The obtained residue was taken in to a mixture of ethanol:water (7:3) mixture and cooled to 0° C. The precipitated solid was filtered and dried under vacuum to afford (2R,3R)-2-(2,4-Difluorophenyl)-3-(4-methylene-1-piperidinyl)-1-(1H-1,2,4-triazol-1-yl)-2-butanol (HPLC purity=99.96%).

Example 7: Preparation of (2R,3R)-2-(2,4-Difluorophenyl)-3-(4-methylene-1-piperidinyl)-1-(1H-1,2,4-triazol-1-yl)-2-butanol To a suspension of 4-methylene-piperidine hydrochloride (7.9 gm) in dichloromethane (80 ml) was added powdered potassium hydroxide (5.5 gm) and stirred. The reaction mixture was filtered and the filtrate was concentrated. The obtained oil was dissolved in 100 ml toluene and to it lithium bromide (5.19 gm) and 1-{[2-(2,4-dimethylphenyl)oxiran-2-yl]methyl}-1H-1,2,4-triazole (5 gm) was added at about 25° C. The reaction mass was heated to 85° C. for 20 hrs. On completion of the reaction, the reaction mass was cooled to 25-30° C. followed by addition of water. The layers were separated. The toluene layer was concentrated under vacuum to obtain a residue. To the residue Para-toluenesulphonic acid monohydrate (4.9 gm) and isopropyl alcohol (20 ml) were added and it was heated to 70° C. to get clear solution. The reaction mixture was cooled to 20-25° C. and stirred. The precipitated solid was filtered and dissolved in dichloromethane and aqueous solution of potassium carbonate (5 gm) was added. After layer separation, methylene dichloride layer was concentrated under vacuum to afford a residue. The residue was taken in a mixture of ethanol:water (7:3) mixture and cooled to 0° C. to get precipitate. The precipitated solid was filtered and dried under vacuum to obtain (2R,3R)-2-(2,4-Difluorophenyl)-3-(4-methylene-1-piperidinyl)-1-(1H-1,2,4-triazol-1-yl)-2-butanol. (HPLC purity=98.70%)

Example 8: Preparation of (2R,3R)-2-(2,4-Difluorophenyl)-3-(4-methylene-1-piperidinyl)-1-(1H-1,2,4-triazol-1-yl)-2-butanol (comparative example)

In an RBF, (2R,3S)-2-(2,4-difluorophenyl)-3-methyl-2-[(1H-1,2,4-triazole-1-yl)methyl]oxirane (17.59 gm) was dissolved in an aqueous solution of 4-methylenepiperidine (113 g, content 61%) and the obtained solution was refluxed at 90° C. The reaction did not proceed to completion even after 48 Hrs. The excess of 4-methylenepiperidine was removed under vacuum, and the residue was dissolved in isopropyl alcohol and thereto was added p-toluenesulfonic acid monohydrate (13.32 g) dissolved in isopropyl alcohol. The obtained mixture was allowed to stand for 1 hour at 45-50° C. and thereafter overnight at 20-25° C., but no crystal precipitated.

The invention claimed is:

1. A process for the preparation of (2R,3R)-2-(2,4-difluorophenyl)-3-(4-methylene piperidin-1-yl)-1-(1H-1,2,4-triazol-1-yl)butan-2-ol [efinaconazole], a compound of formula I,

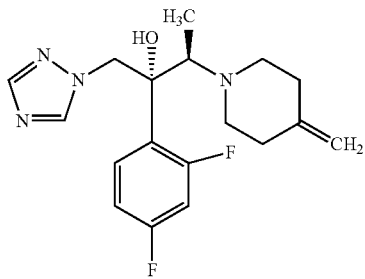

I the process comprising:
(a) reacting (2R,3S)-2-(2,4-difluorophenyl)-3-methyl-2-[(1H-1,2,4-triazol-1-yl)methyl]oxirane, a compound of formula II, with 4-methylenepiperidine, a compound of formula III or salt thereof, to obtain crude efinaconazole;

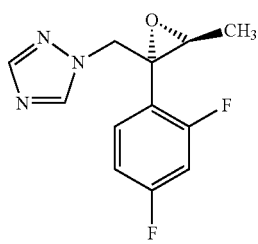

II

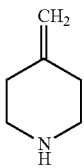

III (b) reacting the crude efinaconazole obtained from step (a) with an optically active acid to obtain a reaction mixture containing an acid addition salt of (2R,3R)-2-(2,4-difluorophenyl)-3-(4-methylene piperidin-1-yl)-1-(1H-1,2,4-triazol-1-yl)butan-2-ol, wherein the optically active acid is di-p-toluoyl tartaric acid;
(c) separating the acid addition salt of (2R,3R)-2-(2,4-difluorophenyl)-3-(4-methylene piperidin-1-yl)-1-(1H-1,2,4-triazol-1-yl)butan-2-ol from the reaction mixture; and
(d) converting the acid addition salt of ((2R,3R)-2-(2,4-difluorophenyl)-3-(4-methylene piperidin-1-yl)-1-(1H-1,2,4-triazol-1-yl)butan-2-ol) to (2R,3R)-2-(2,4-difluorophenyl)-3-(4-methylene piperidin-1-yl)-1-(1H-1,2,4-triazol-1-yl)butan-2-ol.

2. The process as claimed in claim 1, wherein a content of a (2S,3S) isomer of efinaconazole, a compound of formula IV, and/or a (2R,3 S) isomer of efinaconazole, a compound of formula V, and/or a (2S,3R) isomer of efinaconazole, a compound of formula VI

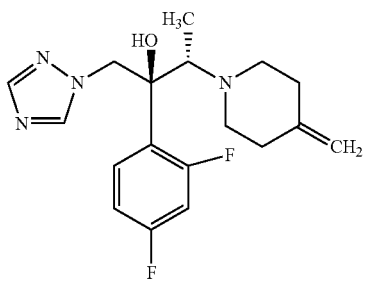

IV

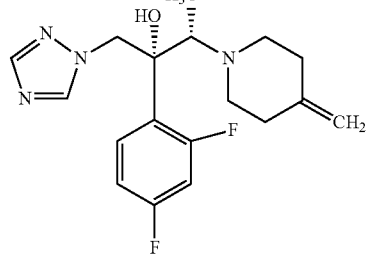

V

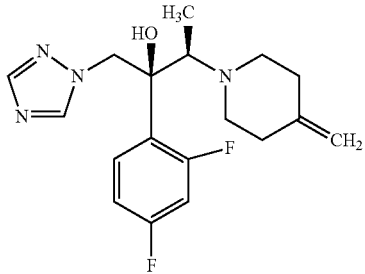

VI is less than 0.5% w/w with respect to efinaconazole as determined by HPLC.

3. The process as claimed in claim 1, wherein the step (a) is carried out in presence of a Lewis acid.

4. The process as claimed in claim 1, wherein the step (a) is carried out in presence of a solvent.

5. The process as claimed in claim 1, wherein the step (a) is carried out in presence of a phase transfer catalyst.

6. The process as claimed in claim 1, wherein the step (a) is carried out in presence of a Lewis acid selected from the group consisting of lithium bromide, boron trifluoride etherate, zinc chloride, ferric chloride, aluminium chloride, lithium perchlorate and stannic chloride, copper(II) trifluoromethanesulfonate, zinc acetate, and zinc trifluoromethanesulfonate.

7. The process as claimed in claim 1, wherein the (2R, 3R)-2-(2,4-difluorophenyl)-3-(4-methylene piperidin-1-yl)-1-(1H-1,2,4-triazol-1-yl) butan-2-ol, the compound of formula I,

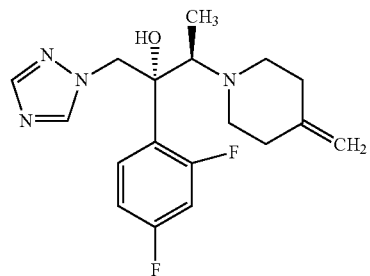

is prepared by a process comprising the step of reacting (2R,3S)-2-(2,4-difluorophenyl)-3-methyl-2-[(1H-1,2,4-triazol-1-yl) methyl] oxirane, a compound of formula II, with 4-methylenepiperidine, a compound of formula III or salt thereof, in the presence of a Lewis acid.

* * * * *